United States Patent
Qureshi

(10) Patent No.: US 9,101,736 B2
(45) Date of Patent: Aug. 11, 2015

(54) EXTERNAL LOOP FOR EXCHANGING CATHETERS AND DELIVERY DEVICES OVER EXCHANGE LENGTH WIRES DURING CATHETER BASED PROCEDURES

(76) Inventor: Adnan Iqbal Qureshi, Edina, MN (US)

(*) Notice: Subject to any disclaimer, the term of this patent is extended or adjusted under 35 U.S.C. 154(b) by 0 days.

(21) Appl. No.: 13/297,957

(22) Filed: Nov. 16, 2011

(65) Prior Publication Data

US 2012/0220983 A1  Aug. 30, 2012

Related U.S. Application Data

(60) Provisional application No. 61/457,320, filed on Feb. 25, 2011.

(51) Int. Cl.
*A61M 31/00* (2006.01)
*A61M 25/01* (2006.01)

(52) U.S. Cl.
CPC .................................. *A61M 25/0169* (2013.01)

(58) Field of Classification Search
CPC ...................... A61M 25/0111; A61M 25/0113; A61M 25/09041; A61M 25/09
USPC ..................... 604/510, 528, 585, 161, 164.05, 604/165.01, 165.02, 167.06, 516, 523; 606/108, 194; 600/104, 434; 607/115; 242/388.6; 623/1.11, 1.12
See application file for complete search history.

(56) References Cited

U.S. PATENT DOCUMENTS

| | | |
|---|---|---|
| 5,139,032 A | 8/1992 | Jahrmarkt et al. |
| 5,324,306 A * | 6/1994 | Makower et al. ............. 606/213 |
| 5,339,833 A | 8/1994 | Berthiaume et al. |
| 5,454,785 A | 10/1995 | Smith |
| 5,843,002 A | 12/1998 | Pecor et al. |
| 5,849,016 A | 12/1998 | Suhr |
| 5,976,154 A | 11/1999 | Suhr |
| 6,086,008 A | 7/2000 | Gray et al. |
| 6,569,106 B1 | 5/2003 | Ullman |
| 6,746,466 B2 | 6/2004 | Eidenschink et al. |
| 7,621,880 B2 | 11/2009 | Ryan et al. |
| 2006/0253048 A1* | 11/2006 | Jones et al. .................... 600/585 |
| 2010/0010475 A1 | 1/2010 | Teirstein et al. |

OTHER PUBLICATIONS

"Knob." Merriam-Webster Dictionary. Accessed online May 15, 2013. <http://www.merriam-webster.com/dictionary/knob>.*
"Push Button." Merriam-Webster's Learner's Dictionary. Accessed online May 15, 2013. <http://www.learnersdictionary.com/search/push+button>.*

* cited by examiner

*Primary Examiner* — Scott Medway
(74) *Attorney, Agent, or Firm* — Nikolai & Mersereau, P.A.; C. G. Mersereau

(57) ABSTRACT

A method and device for exchanging catheters and microcatheters over exchange length wires is disclosed. The device consists of a hollow tube in a loop configuration attached to a base in which the extracorporeal segment of an exchange-length guidewire is inserted. The superior aspect of the tubular loop has a longitudinal slit which allows to and fro movement of catheters using a catheter holder having a handle that protrudes through the slit for easy manipulation.

3 Claims, 5 Drawing Sheets

EXTERNAL LOOP FOR EXCHANGING CATHETERS AND DELIVERY DEVICES OVER EXCHANGE LENGTH WIRES DURING CATHETER BASED PROCEDURES

This application is a non-provisional application of Application No. 61/457,320, filed Feb. 25, 2011 and claims priority from that application which is also deemed incorporated by reference in its entirety in this application.

STATEMENT REGARDING FEDERALLY SPONSORED RESEARCH OR DEVELOPMENT

Not applicable

BACKGROUND OF THE INVENTION

I. Field of the Invention

The present invention relates generally to an extra-corporeal medical device and method to facilitate exchange of catheters and delivery devices during catheter based procedures requiring a plurality of catheters.

II. Related Art

Guidewires are routinely and extensively used in a variety of medical procedures that include the introduction of a catheter into the vascular system of a patient. In many cardiovascular procedures, for example, a guide catheter with a central guidewire advanced through the vascular system until the site to be treated is reached. Thereafter, the initial or guide catheter may be removed and replaced with another over-the-wire (OTW) catheter designed to perform the therapeutic procedure. During such a procedure, it is often necessary to change the catheter while the guidewire remains in place.

Thus, exchanging catheters and delivery devices has become the essence of catheter-based procedures. Catheters vary in diameter from about 0.008 to about 0.087 inches and the length ranges from 70 to 150 cm. Delivery devices include stents and coil delivery systems ranging in diameter from 0.50 to 1 inch and length up to 150 cm.

Currently, as indicated, the vessels of interest are first accessed by small flexible guide catheters. These catheters have limited ability to perform therapeutic procedures and have to be replaced with larger diameter stiffer catheters which lack the structural flexibility and maneuverability required to access tortuous vessel paths as the primary catheter. Once the guide catheter is in position, the exchange length wire has been placed in a desired vascular segment. Once the exchange length wire is in position, the guide catheter is pulled back over the wire.

The exchange length guidewire includes two segments, an intracorporeal segment and an extracorporeal segment. The intracorporeal segment is the portion of the guidewire that resides in the human vascular system during a procedure. The majority of this segment is either covered by a catheter or lying freely in the intravascular compartment. The proximal portion is covered by an insertion sheath or similar device usually placed in the femoral artery. The insertion sheath may contain a Tuohy Buorst device, or the like, to seal the entry into the vascular system. The extracorporeal segment refers to the portion that is outside of the patient's body and exits through the insertion sheath or hub of the catheter.

The extracorporeal proximal portion of the guidewire that protrudes from the vascular system of the patient must be longer than the length of the over-the-wire (OTW) catheter to enable the guidewire to be held when it exits the guidewire lumen of the OTW catheter prior to the distal end of the OTW catheter entering into the vasculature. This enables one to hold the guidewire first at a point distal to the catheter and later at a point proximal to the catheter when the guidewire exits from the proximal end of the guidewire lumen of the OTW catheter. Because of this, the overall length of a guidewire required to advance an OTW catheter over a prepositioned guidewire must be greater than the length of the segment of the guidewire pre-positioned within the vasculature.

The catheter exchange task requires the guidewire to be stabilized manually and the catheter to be replaced to be retracted gently without displacing the wire. The wire/catheter system has to be kept under constant tension in a straight trajectory with no redundancy to avoid displacing the exchange length wire. The insertion sheath through which the catheter and wire are placed also needs to be stabilized during the procedure.

In a typical exchange procedure, once approximately 10-20 cm of the catheter is outside the insertion sheath, one individual (operator #1) continues to move back pulling the catheter while holding the wire stable in increments. Another individual (operator #2) stabilizes the insertion sheath, and activates and reviews the fluoroscopic monitor. Once the catheter is completely out of the insertion sheath, the operator #2 grabs the unsheathed wire, while operator #1 continues to pull the catheter until it is completely removed. Subsequently, the new catheter is advanced on the wire. Operator #1 holds the proximal end of the wire and stabilizes the proximal end of the catheter while it moves forward. Operator #1 must move forward with the advancing catheter to have appropriate control of the wire. The operator #2 pushes the catheter forward through the introducer sheath while activating and reviewing the fluoroscopic monitor until 10-20 cm of the proximal portion of the catheter remain outside the insertion sheath allowing the operator #2 to control both the wire and the catheter. As is apparent, the procedure is cumbersome, requires two operators, and the need for extensive use of a fluoroscope may result in relatively high doses of radiation to a patient.

Thus, it would present a distinct advantage if the exchange of over-the-wire (OTW) catheters and the accompanying delivery devices during catheter-based procedures could be facilitated and simplified and rapidly preformed by a single operator.

SUMMARY OF THE INVENTION

The present invention meets the above-described need by providing a method to exchange catheters and microcatheters over exchange length wires ranging in diameter from 0.008 to 0.38 inches. The device consists of a hollow tube in a loop configuration attached to a base such as a board for stability. The superior aspect of the tubular loop has a longitudinal slit which allows to and fro movement of catheters using a catheter holder having a handle that protrudes through the slit for easy manipulation. The extracorporeal segment of the exchange-length guidewire is inserted in the hollow tubular loop. The proximal end of the guidewire exits through the outlet of the tubular loop and is fixed in place on the base support or board manually or using a releasable wire lock fixed to the base. This arrangement greatly reduces the space necessary to accommodate the extracorporeal segment of the exchange-length guidewire and facilitates catheter exchange with the distal end of the exchange-length wire placed intravascularly at the desired vascular segment through a pre-existing catheter. The pre-existing catheter can be withdrawn over the wire and removed. The catheter is grabbed at its proximal end manually and introduced by retrograde movement over the fixed wire into the tubular loop. The inner diameter of the tubular loop is large enough to allow retrograde movement of the catheter through its central lumen without resistance. The catheter is grabbed by a holder once it enters the tubular loop and moved in a retrograde direction until the proximal portion exits from the outlet of the tubular loop. The catheter is then completely retracted over the fixed wire, the end of which is released from the lock to accommodate the catheter. Subsequently, the new or replacement catheter is advanced through the outlet of the tubular loop over the wire and subsequently into the intravascular compartment with the proximal end of the guidewire relocked after passage of the replacement catheter. In this manner, the tubular loop greatly reduces the space required for completion of exchanges and allows a single operator to easily and rapidly perform the procedure.

BRIEF DESCRIPTION OF THE DRAWINGS

In the drawings wherein like characters denote like parts throughout the same.

DETAILED DESCRIPTION

The following detailed description illustrates one or more specific embodiments in which the invention may be practiced. The description is intended to present the process by way of example and is not intended to limit the scope of the inventive concepts.

Figure 1:
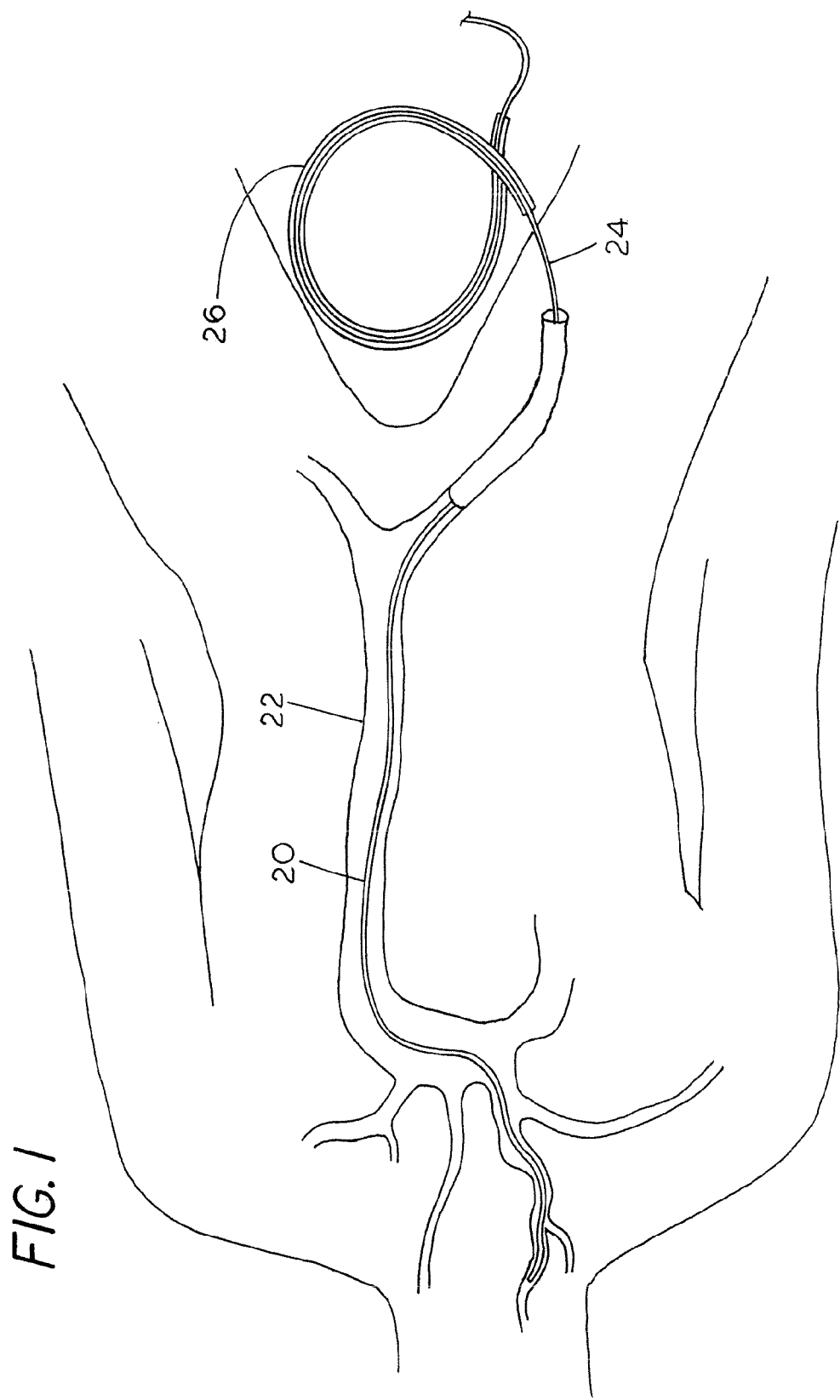
FIG. 1 depicts the intra- and extra-corporeal portion of the exchange length wire.
Figure 2:
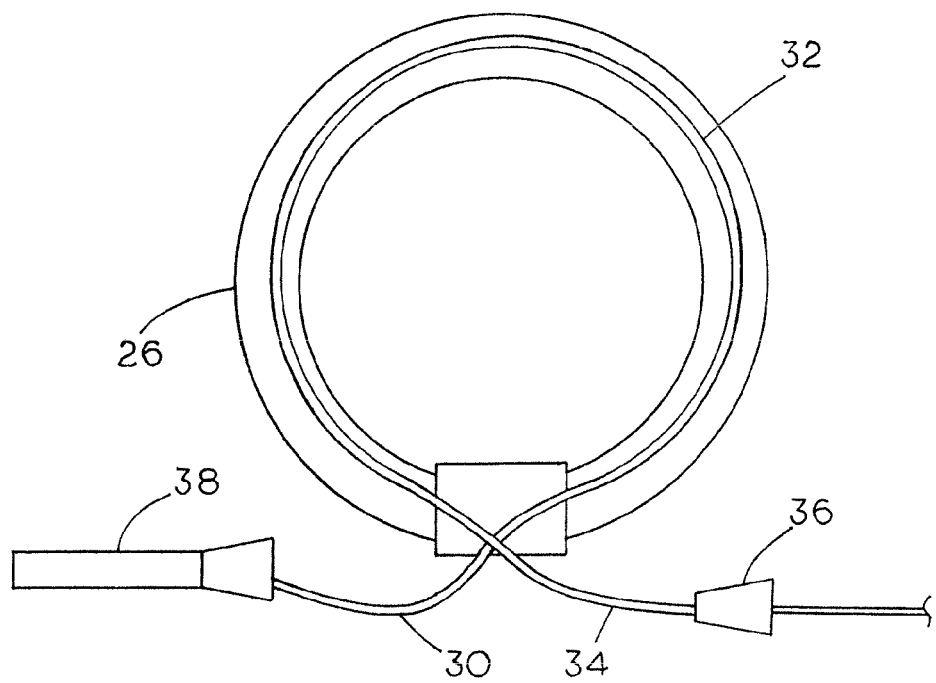
FIG. 2 depicts the pre-, intra-, and post-loop segments of the extracorporeal portion of the exchange length wire.
Figure 3:
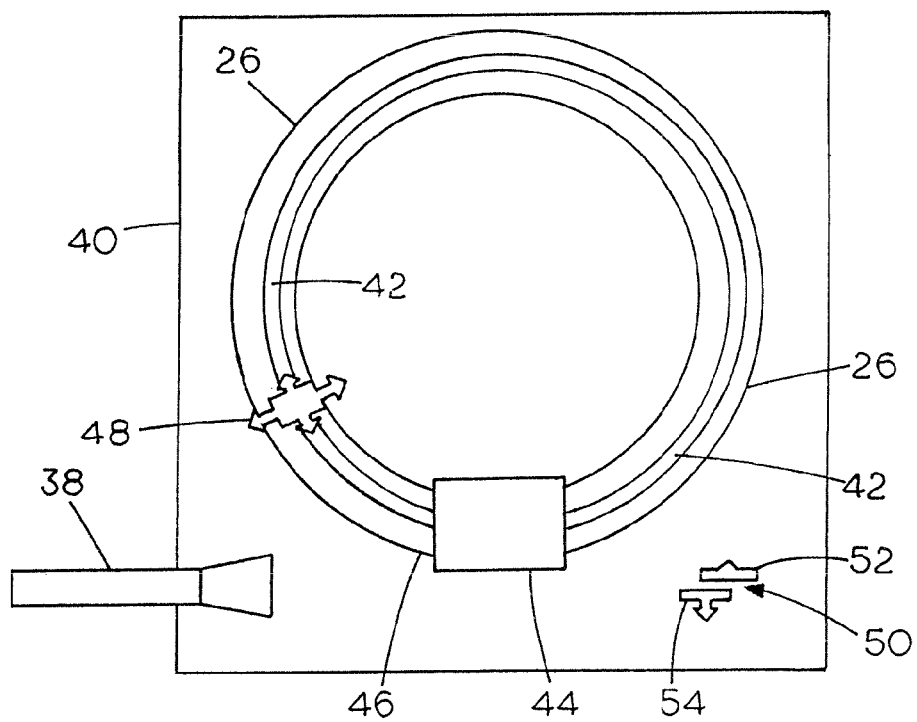
FIG. 3 depicts an enlarged view from the superior aspect of the tubular exchange loop demonstrating the slit on the superior aspect which allows the catheter holder to move in antereo- and retrograde directions.

FIGS. 1 and 2 demonstrate the intracorporeal and extracorporeal segments of the exchange length wire during a tubular loop assisted exchange as they might appear. In FIG. 1, the intracorporeal portion 20 of the guidewire is shown within the human body in the lumen of blood vessels 22 and the extracorporeal segment is shown at 24. An exchange loop is shown at 26. The majority of the intracorporeal segment is either covered by a catheter or lying freely in the intravascular compartment. FIG. 2 is an enlarged schematic view that illustrates the looped extracorporeal segment of the guidewire 24 which is divided into three segments. They include a pre-loop (30) which is the segment between the intracorporeal portion and entry into the loop 21; an intra-loop 32 which is the segment that is encased within the tubular loop 26; and a post-loop section 34. The segment that exits from the loop and may be fixed to the platform board at 36 during exchange process using a locking device 50 (FIG. 3). An insertion sheath is shown at 38.

FIG. 3 depicts a top view of the tubular loop 26 mounted on a base or board 40. The loop may assume an inverted alpha shape or another convenient shape could be used. The tubular loop is preferable made of an inert hollow plastic material with a diameter of about 1 inch (2.54 cm) and a wall thickness of about 2 mm. The loop 26 is adhesively attached to the top surface of the base or flat board 40. The tubular loop 26 has a diameter of about 12 inches (30.5 cm) and includes a slit 42 along the superior aspect of the loop 26 which extends throughout the length of the loop. The inlet to the loop is shown at 44 and the outlet at 46. A catheter clamp or holder is shown at 48 and a type of guidewire lock is shown at 50.

Figure 4:
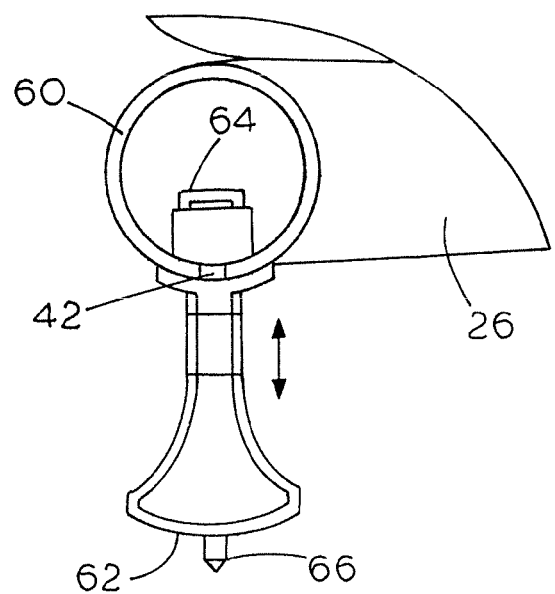
FIG. 4 is an enlarged cross-sectional view of the tubular exchange loop focusing on the catheter holding holder that moves the catheter through the inner lumen of the tubular exchange loop.
Figure 5:
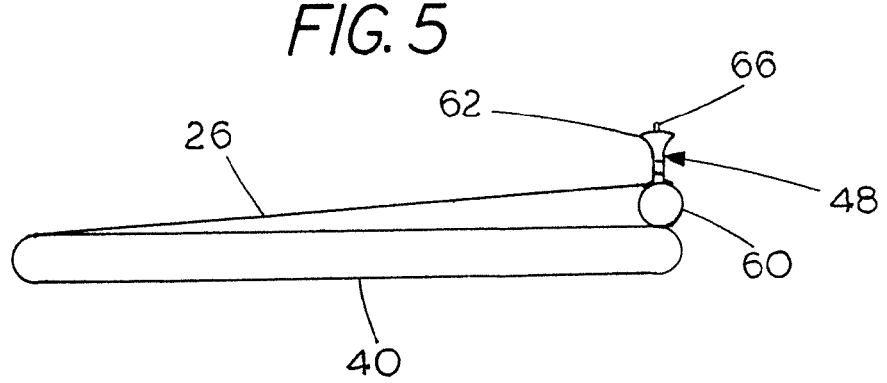
FIG. 5 is an enlarged cross-sectional view of the tubular exchange loop focusing on the catheter holding holder and its relationship to the platform board.

FIGS. 4 and 5 show additional details of a catheter clamp or catheter holder 48. As can be seen from the figures, the holder 48 is partially within the lumen of the tubular loop 26 and partly outside the tubular loop and extends generally at a right angle to the central axis of the lumen. The catheter holder includes a ring or catheter holder loop 60 which may be made of metal or plastic and is generally non-compressible. The loop has a nominal diameter of about 0.75 in (1.9 cm). The catheter holder further includes an operable knob 62 which extends outside the slit 42 and can be used to depress a catch member 64. The holder loop is large enough to ensure passage of the proximal hub of an over-the-wire catheter, after which the knob 62 can be depressed to lock the catheter or hub within the loop of the holder.

The external aspect of the holder comprises the operable handle knob 62 which may be shaped like an inverted pear. Pressing down on the handle pushes the knob inwards locking the catheter. There is a small central push-button knob 66 on the handle to release the locking mechanism.

Figure 6:
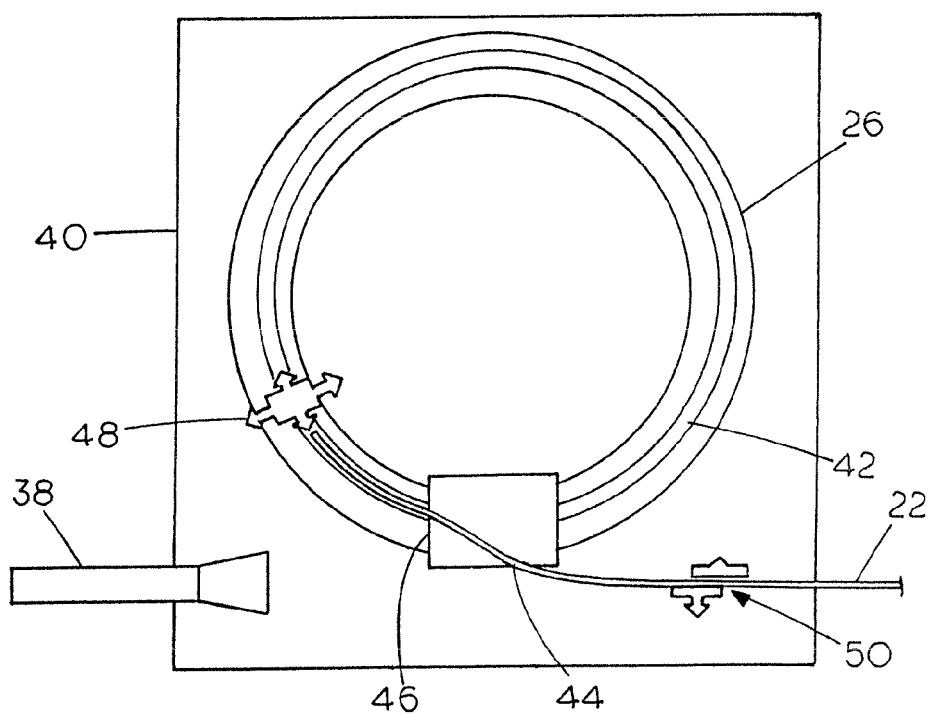
FIG. 6 depicts the proximal end of the exchange length wire fixed by a metal or plastic wire lock after exiting through the outlet of the tubular exchange loop.

FIGS. 3 and 6 illustrate a metal or plastic wire lock 50 in proximity to the outlet 46 of the tubular loop 26. The exchange length wire is introduced through the inlet 44 within the loop of the holder and subsequently introduced through the top slit 42. The proximal end of the wire is secured after it exits the outlet of the tubular loop. The lock 50 may be made of metal or plastic strips 52, 54 with a thickness of about 0.5 inch (1.27 cm) that can be locked together by a screw mechanism such as a set screw, or the like, in the transverse axis. The lock is grounded on the board 40.

Figure 7:
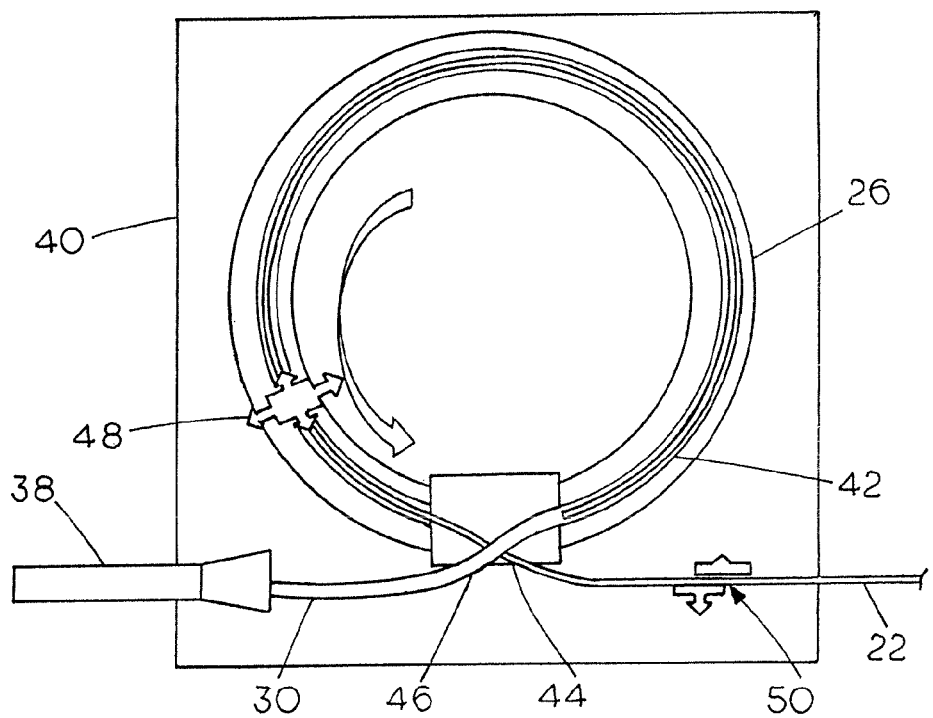
FIG. 7 depicts the catheter being retracted by the catheter holding holder through the tubular exchange loop.

FIG. 7 illustrates a catheter being retracted by the catheter holder 48 through the tubular loop 26 over a fixed wire 22. The holder is able to move freely through and along the slit without resistance after locking down on the catheter body or hub. The catheter is retracted until the guidewire is exposed at the proximal end just outside the insertion sheath 38. The guidewire can then be manually secured at the location of the newly exposed segment of the wire outside the insertion sheath. The catheter can then be pulled back until it is completely off the exchange length guidewire with the proximal end of the guidewire released from the wire lock 50.

Figure 8:
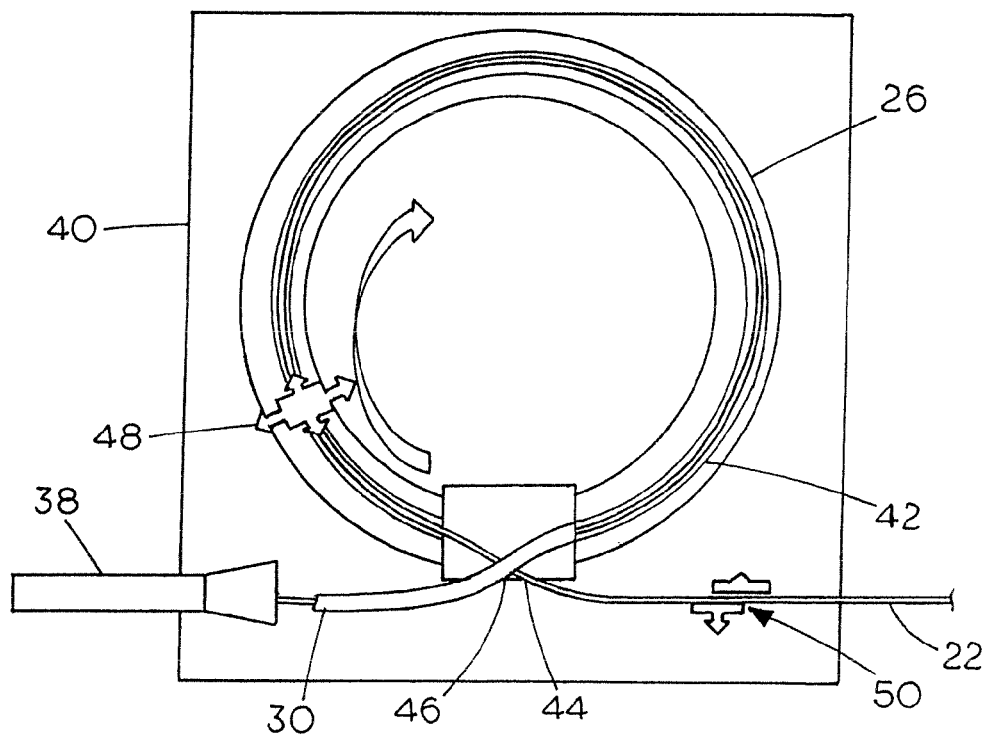
FIG. 8 depicts the new catheter being introduced over the exchange length wire into the tubular exchange loop and being advanced by the catheter holder through the tubular exchange loop.

FIG. 8 demonstrates how the new or replacement catheter is introduced over the exchange length wire into the tubular loop. Once the catheter is over the wire, the catheter is advanced through the outlet of the loop. The distal end of the catheter is held by the holder 48. The catheter is advanced while the proximal end is manually held until the distal end is exposed. The proximal end of the exchange length wire is then secured to the wire lock 50 fixed to the board. The catheter is advanced over the fixed wire through the insertion sheath until it reaches the desired location within the vessel. The external tubular loop is removed after completion of the exchange.

Figure 9:
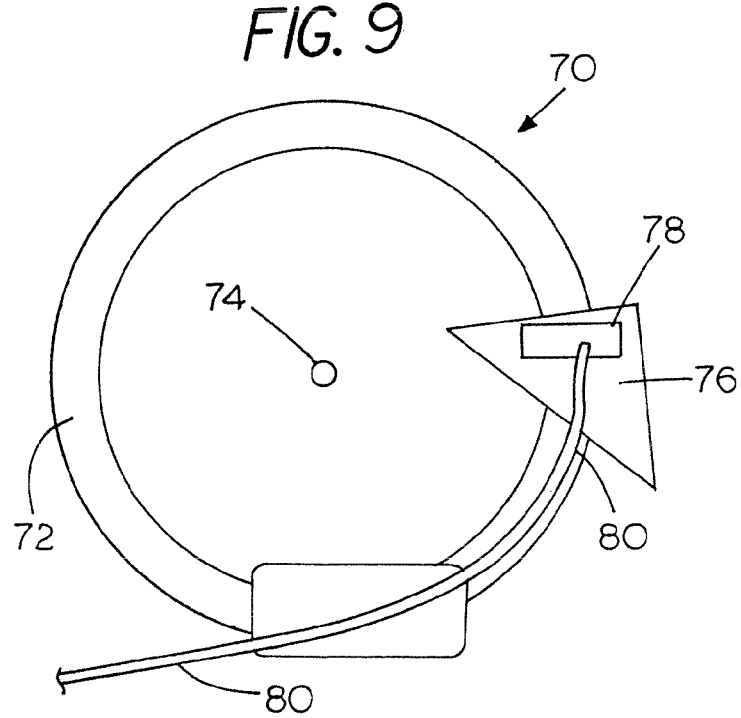
FIG. 9 depicts a plastic lid covering an exchange loop with a central attachment and triangular aperture.

FIG. 9 depicts a circular cover or lid member 70 designed to cover an exchange loop 72 and rotate about a central attachment axis 74. The lid member 70 further is provided with an aperture 76 which may be triangular in shape and which accommodates hemostatic valves 78 or the like attached to an associated catheter 80 during the exchange process. In this embodiment, the tubular exchange loop is large enough to retain the catheter within the loop during the exchange process. The catheters are moved along by rotating the lid member.

It should be noted that the combination of the tubular loop and the catheter holder allow forward and backward motion of an attached catheter, a part of which is in the tubular loop with a high degree of precision. An important factor is that the catheter holder locks down on the catheter without adding any additional traction on the exchange wire.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. An extracorporeal catheter exchange device comprising:
   (a) a tubular loop for accepting an extracorporeal segment of a continuous exchange-length guidewire passed therethrough, but not fixed thereto, and having a surface slit extending therealong; and
   (b) a catheter holder associated with, but independent of, said tubular loop and independent of a catheter to be moved along said loop, said catheter holder having an aspect inside said tubular loop that includes a ring and catch member that moves radially for capturing and releasing a catheter device to be moved along said loop within the ring, and wherein said catheter holder extends through said surface slit and includes an operable knob external to said tubular loop for operating said catheter holder, to both capture and release a catheter device and move a catheter device along said loop, said catheter holder being freely moveable along said tubular loop; wherein depressing said operable knob moves said catch member radially inward to capture a catheter within said ring and wherein said operable knob further comprises a pushbutton release device which, when depressed, releases said catch member to move radially outward thereby releasing a captured catheter.

2. An extracorporeal catheter exchange device as in claim 1 wherein said tubular loop is fixed to a base and an inlet and an outlet for an extracorporeal guidewire segment are on the same side of the tubular loop.

3. An extracorporeal catheter exchange device as in claim 2 further comprising locking device for locking the proximal end of said exchange-length guidewire to said base.

* * * * *